United States Patent [19]

Srivastava et al.

[11] Patent Number: 5,225,181
[45] Date of Patent: Jul. 6, 1993

[54] RADIOLABELED ANTIPLATELET MONOCLONAL ANTIBODY FOR IMAGING IN-VIVO THROMBI

[75] Inventors: Suresh C. Srivastava, Setauket; Barry S. Coller, Dix Hills; George E. Meinken, Middle Island, all of N.Y.

[73] Assignee: The Research Foundation of State University of New York, Albany, N.Y.

[21] Appl. No.: 826,650

[22] Filed: Jan. 21, 1992

Related U.S. Application Data

[63] Continuation of Ser. No. 274,744, Nov. 14, 1988, abandoned, which is a continuation of Ser. No. 742,187, Jun. 7, 1985, abandoned.

[51] Int. Cl.$^5$ .................... A61K 49/02; A61K 39/395
[52] U.S. Cl. .................................. 424/1.1; 530/391.3; 435/240.27; 935/107
[58] Field of Search ............................ 424/1.1, 85.8; 530/391.3, 388.7; 435/70.21, 172.2, 240.26, 240.27; 436/548; 935/103, 104, 107, 110

[56] References Cited

U.S. PATENT DOCUMENTS

| | | | |
|---|---|---|---|
| 4,472,509 | 9/1984 | Gansow et al. | 424/1.1 |
| 4,783,330 | 11/1988 | Furie et al. | 424/1.1 |
| 4,820,505 | 4/1989 | Ginsberg et al. | 424/1.1 X |
| 4,990,326 | 2/1991 | Noujaim et al. | 424/9 |

OTHER PUBLICATIONS

Di Minno et al., *Blood*, vol. 61, No. 1, pp. 140–148 (1983).
Kornecki et al., *Thrombosis Research*, vol. 34, pp. 35–49, (1984).
Coller, *J Clin Invest*, vol. 72, pp. 325–338 (1983).
Coller et al., *J. Lab and Clin. Med.*, vol. 107, No. 4, pp. 384–392 (1986).
"Monoclonal Ab Therapy for Heart Attacks", in *Genetic Engineering News*, vol. 9, No. 2, p. 1 (1989).
Yasuda et al., *J. Clin Invest.*, vol. 81, pp. 1284–1291 (1988).
Mickelson et al., *Circulation*, vol. 81, No. 2, pp. 617–627 (1990).
Pidard et al., *J. Biol. Chem.*, vol. 258, No. 20, pp. 12582–12586 (1983).
Oster et al., *PNAS, USA*, vol. 82, pp. 3465–3468 (1985).
Marchalonis et al., *Antibody as a Tool*, John Wiley and Sons, N.Y., pp. 224 and 456 (1982).
Bennett et al., *PNAS, USA*, vol. 80, pp. 2417–2421, (1983).
Vainchenker et al., *Blood*, vol. 59, No. 3, pp. 514–521 (1982).
Som et al., *J. Nucl. Med.*, vol. 27, pp. 1315–1320, (1986).
Breddin, *Sem. in Thrombosis and Hemostasis*, vol. 15, No. 2 (1989).
Stuttle et al., *Nucl. Med. Comm.*, vol. 9, pp. 647–655 (1988).
Stuttle et al., *Nucl. Med. Comm.*, vol. 9, pp. 813–815 (1988).
Oster et al., *AJR*, vol. 152, pp. 253–260 (1989).
Oster et al., *Radiology*, vol. 171, No. 3, pp. 653–656 (1989).
Valone et al., *Nucl. Med. Biol.*, vol. 15, No. 4, pp. 439–450 (1988).
Thurlow, P. J. et al., *Br. J. Haematol.*, vol. 55, No. 1, pp. 122–134 (1983).

(List continued on next page.)

*Primary Examiner*—Robert L. Stoll
*Assistant Examiner*—John Covert
*Attorney, Agent, or Firm*—Morgan & Finnegan

[57] ABSTRACT

There is provided a radiolabeled monoclonal antibody of the class IgG$_1$ which reacts readily with both normal human and dog blood platelets while failing to react with thrombasthenic human platelets. This antibody has the property of completely blocking interaction of fibrinogen with platelets induced by ADP, and the ability to detect fresh thrombi in vivo.

7 Claims, No Drawings

OTHER PUBLICATIONS

"A Murine Monoclonal Antibody that Completely Blocks the Binding of Fibrinogen to Platelets Produces a Thrombasthenic-like State in Normal Platelets and Binds to Glycoproteins 11b and/or 111a" by Barry S. Coller et al. *J. Clin. Invest.*, 72(1), 325–38, 1983.

"Inhibition of Fibrogen Binding to Stimulated Human Platelets" Bennett, Joel S. et al *Proc. Natl. Acad. Sci.*, 80(9) 1983, 2417–2421.

*Genetic Engineering News*, vol. 9, No. 2 "Monoclonal Ab Therapies for Heart Attacks" (Feb. 1989).

Yasuda et al., *J. Clin. Invest.*, vol. 81, Apr. 1988, pp. 1284–1291.

Thiagarajan et al., *J. Clin. Invest.*, vol. 75, Mar. 1985, pp. 896–901.

Thiagarajan et al., *American Journal of Hematology*, vol. 14, pp. 255–269 (1983).

Coller, *J. Clin Invest.* vol. 76, pp. 101–108 (1985).

RADIOLABELED ANTIPLATELET MONOCLONAL ANTIBODY FOR IMAGING IN-VIVO THROMBI

This invention was made with Government support under Grant No. HL-19278 awarded by National Institute of Health. The Government has certain rights in the invention.

This is a continuation of co-pending application Ser. No. 274,744, filed on Nov. 14, 1988, now abandoned, which is a continuation of co-pending application Ser. No. 06/742,187, filed on Jun. 7, 1985 now abandoned.

CROSS REFERENCE TO RELATED APPLICATIONS

This application is related to application Ser. No. 07/247,627 entitled FIBRINOGEN BLOCKING MONOCLONAL ANTIBODY, filed on Nov. 22, 1988 pending, which is a continuation application of Ser. No. 06/742,208, filed concurrently on Jun. 7, 1985, now abandoned.

BACKGROUND OF THE INVENTION

The problems inherent in precisely determining the anatomic location and extent of the thrombus in thrombovascular disease are well known. Many techniques have been developed for the purpose. Imaging the thrombus with radiolabeled fibrinogen and various other radiopharmaceuticals have been found insufficiently sensitive and/or specific. The use of platelets directly labeled with radioactive nuclides has been attempted; however, this technique has also not gained widespread use because of the complexity of the labeling procedure. Furthermore the low target to background ratios often require either delayed imaging or background subtraction to obtain suitable results.

Radiolabeling techniques for proteins are well known. Many radiolabels may be used either directly as in the case of, say, sodium $^{125}I$, $^{125}I$ or $^{131}I$, or indirectly wherein the protein is first conjugated with, say, diethylene triamine pentaacetic acid (DTPA) cyclic anhydride, to which indium-111 is then chelated. It would be desirable therefore to provide a simple technique whereby a protein could be radiolabeled with a short-lived nuclide suitable for imaging and this intermediate then coupled to the platelets in such a way that they would bind to the thrombi in sufficient quantity to be located by well known scanning techniques.

Coller et al., (J. Clin. Invest., 72, 325 (1983)) developed a monoclonal antibody (10E5) that completely blocked the binding of fibrinogen to platelets. The three clones having the most potent antibodies as reported on page 327, column 1 of the Coller paper, were not found to react with dog blood platelets. This is not an irrelevant matter, since it is not generally permissible to carry out human testing of a novel pharmaceutical without previous animal testing thereof. Thus, it may not be possible to determine the ultimate human utility of the 10E5 antibody disclosed by coller in his paper because of said regulatory prohibitions. Thus, it would be desirable to provide monoclonal antibodies that not only have the properties of the 10E5 monoclonal antibody but also react with test animal platelets so that in vivo testing thereof prior to human testing, could be carried out.

SUMMARY OF THE INVENTION

Human blood platelets were injected into mice. The mouse spleen was removed and fused with a mouse myeloma by a modification of the technique of Levy et al., (Curr. Top. Microbiol. Immunol., 81, 164 (1978)). The fused cells were incubated and then further incubated in HAT medium (in which non-fused cells will not grow). The cells were then diluted out and screened in a screening assay for antifibrinogen receptor activity. There was selected one particular clone, designated 7E3 of the class $IgG_1$ which reacts with normal human blood platelets and with dog blood platelets, fails to react with thrombasthenic platelets or human platelets whose GPIIb/IIIa complex is disassociated with EDTA, reacts slowly with unactivated human platelets and more rapidly with ADP activated human platelets and completely blocks the interaction of fibrinogen with platelets induced by ADP. These monoclonal antibodies were then radiolabeled with a halogen or metallic radio nuclide. Such labeling may be direct as in the case of $^{125}I$ or $^{123}I$ or indirect as in the case of $^{111}In$ wherein the antibody is conjugated with a chelating agent such as DTPA.

The thus labeled antibody was reacted with autologous blood platelets at a level of concentration insufficient to block all of the fibrinogen binding sites but sufficient to provide a detectable level of radio activity on said platelets. The platelets which were of species compatible blood (i.e., dog blood for dogs, human blood for humans) were then suspended in a suitable suspending medium which is physiologically compatible with proposed subject and injected intravenously. It has been found that thrombi up to at least 10 hours in age will react with said antibody conjugated platelets in a manner that will make the in vivo thrombi detectable by radioscintingraphy. The labeled antibody can also be injected directly into the bloodstream (intravenously) to label platelets in vivo. This approach though operative was less efficient than the ex vivo labeling in dogs, but thrombi could be detected. In view of the demonstrated success in vivo in dogs, the technique is similarly useable in human subjects.

DESCRIPTION OF THE PREFERRED EMBODIMENTS

Citrated platelet-rich plasma were prepared in accordance with the method of Coller et al., (Blood, 47, 841 (1976)), suspended in a suitable buffer and mixed with Freund's complete adjuvent. Injections of between about $1 \times 10^8$ to $5 \times 10^8$ washed platelets were injected six times at weekly intervals into a BALB/c mouse intraperitoneally and a seventh similar injection without adjuvant at a similar time interval was given intravenously. Three days later the mouse was killed, the spleen removed, the cells separated and fused with a BALB/c mouse myeloma line in accordance with the method of Levy et al., (supra). In this method, the spleen cells and the myeloma cells in a ratio of 3.9:1 were pelletted together, the pellet suspended in polyethylene glycol (35%) in RPMI 1640 medium whereupon the cells were immediately centrifuged at low velocity. The solution was then diluted to about 25% of its previous concentration with RPMI 1640, the cells resuspended, recentrifuged and the supernatant removed. The supernatant was then incubated in a 5% $CO_2$ 95% air atmosphere in RPMI 1640 medium supplemented with fetal calf serum and thereafter selection made in the usual manner by adding HAT medium and aliquoting into microtiter wells. After two weeks, the supernatant of the wells that showed growth were screened for antifibrinogen receptor activity. The clones obtained by this method were selected for various qualities; one in particular, 7E3 was selected for certain qualities.

The antibody was isolated from the supernatant in the wells or flasks. Alternatively, the hybridomas were injected intraperitoneally into Pristane$^R$ pretreated BALB/c rats and the antibodies isolated from the ascitic fluid. The antibody was purified by precipitation with 50% saturated ammonium sulfate, resuspended in between 5 and 10% of the original volume in sodium phosphate buffer and dialyzed against the same buffer. Chromatography on protein A-Sepharose CL-4B equilibrated with phosphate buffer was carried out, elution was with phosphate buffer followed by decreasing pH 0.1M citrate buffers. 7E3 antibody was eluted after the pH decreased to about 6.0. Protein elution was as monitored by ultra-violet spectroscopy at 280 nm.

Ouchterlony immuno diffusion analysis against anti-IgG1, IgG2a, IgG2b, IgG3, IgM and IgA sera indicated the exclusive presence of IgG1.

A deposit of the cell line derivative, murine hybridoma 7E3, was made with the American Type Culture Collection, on May 30, 1985. The accession number HB8832 was assigned after successful validity testing and the requisite fees were paid. Access to HB8832 will be afforded the Honorable Commissioner of Patents and Trademarks upon request. All restrictions to availability of said hybridoma to the public will be irrevocably removed upon the issuance of a patent based on this application and said hybridoma will remain permanently available for a period of thirty (30) years after the date of deposit or for a term of at least five (5) years after the most recent request for the furnishing of a sample or the effective life of the aforesaid patent, whichever is longer. Should HB8832 become nonviable or mutate, it will be replaced.

The antibodies themselves may be directly coupled to radiolabels, for example, sodium radio-iodide ($^{123}I$, $^{125}I$, or $^{131}I$) and unradioactive sodium iodide being added to obtain a molar ratio of iodide to antibody of about 0.5 in phosphate buffer at pH 7. The iodinated protein was separated from the unbound, free iodide by column chromatography on P6 gel giving labeling yields between 30 and 80% and specific activities of 20 to 300 uCi/ug. In the labeling with indium ($^{111}In$), DTPA was reacted with the monoclonal antibody in a very substantial excess usually about 50 to 1 molar excess and the unconjugated DTPA removed by dialysis against HEPES/sodium chloride buffer at pH 7. Between 3 and 10 mCi of indium ($^{111}In$) trichloride were added to 100 to 300 ug of the DPTA 7E3 conjugate in an acetate buffer, incubated for 30 minutes at 37° C. and the unbound indium removed by elution through gel columns. Labeling yields of between 60 to 80% and specific activities of 10 to 40 uCi/ug were obtained with final substitution levels of less than 0.2 indium atoms per antibody molecule.

The thus produced antibody labeled with $^{125}I$ was then bound to whole blood samples. Platelet-rich plasma prepared from whole blood was collected into 3.2% sodium citrate and predetermined amounts of antibody of specific activity from between about 20 to about 150 CPM/ng were added to 0.2 ml. of the platelets. Aliquots were incubated for predetermined time periods of between 0.5 and 20 minutes, layered onto silicon oils or 30% sucrose, centrifuged at 12,000 g for 2 minutes to separate the platelets from the unbound antibody and the radioactivity of the samples determined. It was found that binding did not increase after 2 hours contact time. The platelets from dog blood, normal human blood, and from patients with Glanzmann thrombasthenia was tested. It was shown that there was no binding to the latter. When platelets are treated with ADP, the rate of 7E3 binding is far more rapid than with buffer-treated platelets. This testing was carried out with platelet-rich plasma anticoagulated with sodium citrate.

Radioimmunoelectrophoretic analysis was carried out on solubilized platelet proteins with a combination of heterologous anti-platelet antibody and radiolabeled 7E3 antibody. The platelets were solubilized in 1% Triton X-100 and electrophoresed on 1.5% agar gels. The wells contained normal platelets, platelets from a patient with Glanzmann's thrombasthenia, normal solubilized platelets treated with 10 mM EDTA to split the GPIIb/IIIa complex, and contained normal serum. Arcs were developed by overnight incubation with rabbit anti-platelet serum and $^{125}I$ labeled 7E3 antibody. The 7E3 bound to the protein arc in normal platelets but this arc was missing in thrombasthenic platelets and platelets treated with EDTA.

When the platelets were incubated with an excess of the 7E3 monoclonal antibody they showed no interaction with fibrinogen.

In imaging experiments, experimental thrombi were induced by the transcatheter placement of copper coils into certain arteries and veins from 1 to 48 hours before injection of the test material. The test material was prepared by preincubating anticoagulated blood of the species in question, preferably dogs, with approximately 3 mCi of either the $^{123}I$ 7E3 or the $^{111}In$ DPTA 7E3. The images were obtained with a large field-of-view gamma camera and thrombus-to-background and thrombus-to-blood pool ratios were calculated. It was noted that within one minutes after injection, 25 to 30% of the injected activity was cleared from the blood, apparently by the spleen and liver. This clearing increased to a total of 50% by 30 minutes, but thereafter remained fairly constant for 3 to 4 hours, increasing to 78% 24 hours after injection. Venous and arterial thrombi could be visualized as early as 1 to 5 hours after injection. While it was found that 1 through 10 hour old thrombi could be visualized with this technique, 48 hour old thrombi (shown by autopsy) had the same background activity and could not be imaged.

EXAMPLE I

Antibody Production

A BALB/c mouse (Jackson Laboratories, Bar Harbor, Me.) was injected intraperitoneally with six weekly 0.2 ml injections of $3 \times 10^8$ washed platelets (citrated PRP washed twice in 0.15M NaCl, 10 mM Tris/Cl, 10 mM EDTA, pH 7.4 [TS-E]), resuspended in 1/10 to 1/20 of their original volume in TS-E, and mixed 1:1 with complete Freund's adjuvant. The seventh weekly injection was given intravenously into the tail vein and consisted of 0.3 ml. containing $5 \times 10^8$ washed platelets resuspended in T-S without EDTA. Each of the seven platelet suspensions was obtained from a different donor. Three days after the last injection, the mouse was killed by cervical dislocation and the spleen removed. A suspension of spleen cells in RPMI 1640 was prepared by teasing the spleen apart. After erythrocytes were lysed with ammonium chloride, the spleen cells were fused with a nonsecretory BALB/c mouse myeloma cel line (X63-Ag 8.653) that had been kept frozen in 10% MSO, 90% fetal calf serum until one week before fusion, when it was thawed and maintained in the culture medium routinely used (RPMI 1640 supplemental with 10% fetal calf serum and 1,000 U of penicillin and 100 ug of streptomycin/ml). Fusion was carried out according to a modification of the method of Levy et al. (supra). Briefly, $2.7 \times 10^8$ spleen cells and $7 \times 10^7$ myeloma cells were pelleted together, the pellet was gently suspended in 2 ml of 35% polyethylene glycol in RPMI 1640 medium and the cells immediately centrifuged at 500 g at 22° C. for 6 minutes. The solution was then diluted with RPMI 1640 to 9% polyethylene glycol, the cells resuspended and immediately centrifuged at 230 g. for 6 minutes at 22° C. The supernatant fluid was then aspirated and the fused cells suspended in RPMI 1640 medium and supplemented with 20% fetal calf serum and 10% 109 medium (National Collection of Type Cultures). The cells were placed in a flask and incubated overnight at 37° C. in a 5% $CO_2$, 95% air atmosphere. The following day, the medium was made selective for successfully hybridized cells by adding hypoxanthine ($10^{-4}$M), aminopterin ($4 \times 10^{-7}$M), and thymidine ($1.6 \times 10^{-5}$M), after which the cells were aliquoted into 960 microtiter wells (Costar, Data Packaging, Cambridge, Mass.). Two weeks later, 574 wells showed growth and the supernatant fluids from 59 wells were positive in a screening assay for antifibrinogen receptor activity (see below). After an additional two weeks in culture, the positive clones were transferred to 24-well microtiter dishes (Costar) and fed with the same medium as above, but without the aminopterin. The clones were expanded and the cells that continued to produce antifibrinogen receptor antibody were suspended in 90% fetal calf serum-10% DMSO and frozen in liquid nitrogen.

The clones were subclones by both limiting dilution technique and growth in soft agar to insure monoclonality.

Ascitic fluid rich in 7E3 antibody was prepared by intraperitoneal injection of Pristane-pretreated BALB/c mice with $5 \times 10^6$ hybrid cells that had been washed twice in 0.15M NaCl, 10 mM sodium phosphate, pH 7.4 (PBS).

EXAMPLE II

Screening Assay 35 ul of PRP (platelet rich plasma) (adjusted to $3 \times 10^{11}$ platelets/liter) and 35 ul. of the supernatant culture medium (or ascitic fluid) to be assayed were incubated together for 2 minutes in a well of a round-bottomed microtiter plate (Linbro Chemical Co., Hamden, Conn.). 5 ul of the fibrinogen-coated bead suspension was then added and the plate was mixed on a rotator (Tekator V, American Scientific Products, Edison, N. J.) for 5 minutes at 280 rpm. The wells were observed from the bottom with the aid of a magnifying mirror apparatus (Cooke Microtiter System, Dynatech Laboratories, Inc., Alexandria, Va.). Wells containing culture medium that had not been used for growing cells showed marked agglutination of the beads (rated as 4+), whereas the supernatant culture medium or mouse ascitic fluid from positive clones inhibited the agglutination, resulting in lower readings (0-3+).

EXAMPLE III

Antibody Purification

Culture supernatants were precipitated at 4° C. with 50% saturated ammonium sulfate and resuspended to between 1/20 and 1/10 of their original volume in 0.1M sodium phosphate buffer, pH 8.0. After dialysis against the same buffer, the samples were applied to a $0.8 \times 15.9$ cm column of protein A Sepharose CL-4B that had been equilibrated with the phosphate buffer (after having been washed with both the phosphate buffer and a 0.1M citrate buffer, pH 3.0). The column was eluted with the phosphate buffer until the optical density of the eluate returned to base line, after which stepwise elution was accomplished with 0.1M citrate buffers of pH 6.0, 4.5, 3.5 and 3.0, as described by Ey, et al., (Immunochemistry, 15, 429 (1978). 7E3 immunoglobins were eluted at pH 6.0. Protein elution was monitored by optical density at 280 nm and appropriate fractions were pooled and dialyzed against T-S containing 0.05% sodium azide. Antibody concentration was estimated by absorption at 280 nm, assuming A1% =15.

EXAMPLE IV

Antibody Labeling with Radioiodine

To 100 ug of 7E3, first radioiodide ($^{123}$I) and then cold sodium iodide were added to obtain a molar ratio of iodide to antibody of 0.5. Five ug of chloroamine T was added next and the reaction was carried out in phosphate buffer (pH 7.0) in a total volume of 200 ul for 1-3 minutes, after which iodinated antibody was separated from free iodide by chromatography on a column ($0.7 \times 15$ cm) of P-6 gel (BioRad Laboratories, Inc., Richmond, Calif.) or G-25 gel (Pharmacia Fine Chemicals, Piscataway, N.J.). Labeling yields were between 30-80% with the specific activities ranging from 20-300 uCi/ug. The integrity of the antibody after labeling was assessed by both polyacrylamide gel electrophoresis and the fibrinogen-coated bead assay, and the efficiency of separating bound from free iodine was judged by the precipitability of the radioactivity after reaction with 10% trichloroacetic acid.

In accordance with the above procedure Na$^{125}$I or Na$^{131}$I may be used in place of Na$^{123}$I to obtain a similar product.

EXAMPLE V

Antibody Labeling with Indium

Labeling with 111In (6) was performed by the DTPA (diethylenetriaminepentaacetic acid) cyclic anhydride method. The ratio of anhydride to 7E3 was 50:1 and removal of unconjugated DTPA was accomplished by exhaustive dialysis against 0.01M HEPES-0.15M sodium chloride buffer, pH 7. The labeling was carried out by adding 3-10 mCi of $^{111}$In-Cl$_3$ (research grade, Medi-Physics, Inc., Richmond, Calif.) to 100-300 ug of DTPA-7E3 conjugate in a 1 ml. volume of buffer and incubating for 30 minutes at 37° C. The unbound indium was removed by elution through ($0.7 \times 15$ cm) columns of P6 or G-25. The product was characterized by polyacrylamide gel electrophoresis and assayed by the fibrinogen-coated bead agglutination test. Labeling yields ranged between 60-80% and specific activities were 10-40 uCi/ug with a substitution level of less than 0.2 indium atoms per antibody molecule.

EXAMPLE VI

In Vivo Evaluation

The evaluation of $^{123}$I-7E3 and $^{111}$In-DTPA-7E3 was performed in adult female mongrel dogs (20-30 kg body weight). Pentobarbital anesthesia was employed and no heparin was used throughout the experiments. Most imaging experiments were carried out following injection of labeled platelets obtained by pre-incubating $^{123}$I-7E3 (3.0 mCi) or $^{111}$In-DTPA-7E3 (3-3.5 mCi) with 150 ml. of blood anticoagulated with ACD-A (6:1) at 22° C. for 1 hour. Blood clearance studies were performed in normal dogs with doses of 0.5 mCi of $^{123}$I-7E3. A small number of imaging experiments were performed without pre-inoculation. In most experiments the blood was centrifuged (1800 g. at 22° C. for 9 minutes), the plasma containing unbound antibody removed, and the cells resuspended in a 6/1 mixture of saline and ACD-A. In accordance with the above procedure, $^{111}$In labeled 7E3 may be used in place of $^{125}$I-7E3. A small number of imaging experiments were performed without the preincubation step, wherein antibody was injected intravenously to label the platelets in vivo; positive results were also obtained with this technique.

To simulate the in vivo experiments, an in vitro study of incorporation of radiolabeled 7E3 into human blood clots was performed. Two 1 ml samples of whole blood anticoagulated with 0.01 volume of 40% trisodium citrate were incubated with 0.1 ug/ml of $^{111}$In-DTPA-7E3 for 30 minutes at 37° C., after which one sample was centrifuged and the percentage of radioactivity sedimenting with the cellular fraction determined. The second aliquot was added to 1 ml of unanticoagulated whole blood that had been placed into a tube containing bovine thrombin (1 U/ml, Parke-Davis, Morris Plains, N.J.) that had been allowed to clot for 30 minutes at 37° C.; the clot was then washed twice in 0.15M NaCl and counted in a gamma spectrometer.

Experimental thrombi were induced by the transcatheter placement of copper coils into the common carotid, pulmonary and femoral arteries, the jugular and femoral veins, and the right ventricle. Thrombi were induced 1, 2, 3, 4, 8 and 48 hours before injection of the $^{111}$In-DTPA-7E3. Images (0-5.0 hours after injection) were obtained with a large field-of-view gamma camera (Ohio Nuclear, Solon, Ohio) interfaced with a Gamma-11 system (Digital Equipment Corporation, Waltham, Mass.), using a 64×64 matrix. Thrombus-to-background and thrombus-to-blood pool ratios were calculated. For blood clearance determinations, samples were obtained at 1, 2, 3, 4, 5, 10, 15, 20, 30, 45, 60, 90, 120 and 180 minutes as well as 24 hours after injection. Urine samples of the 0-1, 1-2, 2-3, and 3-4 hour periods were assayed for radioactivity. Results were variously expressed as the percentage of injected activity per whole blood volume (7% of body weight) or of injected dose contained in the total urine volume. At the end of the experiments the animals were sacrificed by injecting a 12-20 mg/kg dose of pentobarbital.

EXAMPLE VII

Binding of $^{125}$I Antibody

Binding was assessed at 22° C., using PRP (3×1011 platelets/liter) prepared from whole blood collected into 0.01 volume 40% sodium citrate. Trace doses of the $^{125}$I-7E3 (approximately 0.2 mu g/ml final concentration) were added to 0.2 ml PRP. To establish equilibrium binding conditions, duplicate 0.1 ml aliquots were layered onto silicon oil (Contour Chemical Co., Inc., North Reading, Mass.; specific gravity 1.040) or 30% sucrose after 0.5 for up to 4 hours. They were then centrifuged at 22° C. for 2 minutes at 12,000 g in a microcentrifuge (Beckman Instruments, Inc., Irvine, Calif.) to separate platelets with bound antibody from unbound antibody. The tips containing the platelet pellets were sliced off with a dog nail cutter and both the tip and the supernatant were counted. Binding increased for up to 2 hours with unactivated platelets.

EXAMPLE VIII

Buffer- and ADP-Treated Platelets

Platelet-rich plasma was prepared from blood anticoagulated with 0.01 volume of 40% sodium citrate and gel-filtered. Aliquots (0.2 ml) of the GFP (3.30-3.65×1011 platelets/l) were incubated with either 22 ul of buffer (0.15M NaCl, 0.01M HEPES, pH 7.4) or ADP (5 uM final concentration) for 30 seconds at 22° C. and then 20 ul of various concentrations of $^{125}$I-7E3 to achieve the final concentrations indicated below. After 5 minutes, which is too short a time for equilibrium to be established, duplicate 0.1 ml samples were layered over 0.1 ml 30% sucrose and centrifuged to separate free antibody from platelet-bound antibody.

TABLE 1

| $^{125}$I-7E3 (ug/ml) | Buffer Molecules/Platelet (% Bound) | ADP Molecules/Platelet (% Bound) |
|---|---|---|
| 1.0 | 2,100 (18.6) | 5,600 (44.2) |
| 3.8 | 5,200 (13.2) | 14,300 (36.5) |
| 6.7 | 10,100 (14.6) | 21,300 (30.9) |
| 13.6 | 17,900 (12.8) | 25,500 (18.2) |

EXAMPLE IX

Effect of Prestimulating Platelets with ADP

Platelet-rich plasma (2.84×1011 platelets/l) was prepared from blood anticoagulated with 0.01 volume 40% sodium citrate. Aliquots of 0.2 ml were incubated with 10 ul of buffer (0.15M NaCl, 0.01M HEPES, pH 7.4) or ADP (5 uM final concentration) at 22° C. for the indicated times and then 1 ul of $^{125}$I-7E3 (0.7 ug/ml final concentration) for 2 minutes at 22° C. Free and platelet-bound antibody were separated by centrifugation of duplicate 0.1 ml samples through 0.1 ml of 30% sucrose and the amount of antibody bound to the platelets determined.

TABLE 2

| Buffer | | ADP (5 uM) | |
|---|---|---|---|
| 5 s | 1,960* | 5 sec | 3,570 |
| 20 min | 1,720 | 15 sec | 3,740 |
| | | 30 sec | 3,530 |
| | | 1 min | 3,290 |
| | | 3 min | 3,210 |
| | | 6 min | 3,120 |
| | | 10 min | 2,790 |
| | | 20 min | 2,320 |

*molecules of $^{125}$I-7E3 bound per platelet (mean of duplicate determinations).

EXAMPLE X

Effect of ADP stimulation on the rate of binding of $^{125}$I-10E5 and $^{125}$I-7E3 to gel-filtered platelets.

PRP was prepared from blood collected in 0.01 volume 40% sodium citrate and then gel-filtered in HBMT buffer. Aliquots (0.2 ml) of the resulting suspensions (3.31-3.65×1011 platelets/l) were incubated for 30 seconds with 22 ul of either 0.15M NaCl, 0.01M HEPES, pH 7.4 buffer or 100 uM ADP prepared in the same buffer. Subsaturating concentration of $^{125}$I-10E5 (2 ul; final concentration 2.5 ug/ml) or $^{125}$I-7E3 (4 ul; final concentration 1.0 ug/ml) was then added and at the indicated times. Two 0.1 ml. aliquots were removed from each reaction mixture, layered over 0.1 ml of 30% sucrose and centrifuged at 12,000 g. for 3-4 minutes. The tip containing the platelet pellet was amputated and the radioactivity of both the tip and supernatant assayed. The majority of duplicate values for the percentage bound differed from each other by less than 5% and the greatest difference was 11%. To facilitate comparison, the data are presented as the percentage of the maximal fraction of added radioactivity bound for each antibody, the latter being 74.1% for 7E3 and 50% for 10E5. The differences in total 7E3 and 10E5 bound per platelet reflect differences in input concentrations and affinity. The 10E5 data are the means from two separate experiments and the 7E3 data are from 1 of 11 separate experiments showing an enhanced rate of 7E3 binding to ADP-treated GFP. In other experiments using a lower concentration of $^{125}$I-10E5 (0.7 ug/ml), ADP activation also failed to alter the rate of binding.

We claim:

1. A radiolabelled monoclonal antibody radiolabelled with a halogen or metallic radionuclide selected from the group consisting of $^{123}$I, $^{125}$I, $^{131}$I, $^{111}$In-DTPA, $^{99m}$Tc and $^{97}$Ru, wherein the monoclonal antibody is of the class IgG, produced by a hybridoma formed by fusion of cells from a BALB/C mouse myeloma line, X63.Ag8.653 and spleen cells from a BALB/c mouse previously immunized with human blood platelets, which antibody:
 a) reacts readily with normal human platelets and with dog platelets;
 b) fails to react with thrombasthenic human platelets or human platelets whose GPIIb/IIIa complex is dissociated with EDTA and
 c) reacts slowly with inactivated platelets and substantially twice as rapidly with ADP activated platelets; and
 d) completely blocks the interaction of fibrinogen with platelets induced by ADP.

2. An antibody of claim 1 wherein the radiolabels are selected from the group consisting of $^{123}$I, $^{125}$I, $^{131}$I and $^{111}$In-DTPA.

3. An antibody of claim 1 wherein the radiolabel is $^{123}$I, $^{125}$I or $^{131}$I.

4. An antibody of claim 1 wherein the radiolabel is $^{111}$In-DPTA.

5. A radiolabelled monoclonal antibody of the class IgG$_1$ produced by the hybridoma cell line designated 7E3 having ATCC Accession No. HB8832 wherein the radiolabel is selected from the group consisting of $^{123}$I, $^{125}$I, $^{131}$I and $^{111}$In-DPTA, $^{99m}$Tc and $^{97}$Ru.

6. A radiolabelled monoclonal antibody according to claim 5 wherein the radiolabel is selected from the group consisting of $^{123}$I, $^{125}$I, $^{131}$I and $^{111}$In-DPTA.

7. A radiolabelled monoclonal antibody according to claim 6 wherein the radiolabel is $^{111}$In-DPTA.

* * * * *